United States Patent
Lim et al.

(10) Patent No.: US 10,464,901 B2
(45) Date of Patent: Nov. 5, 2019

(54) COMPOSITION INCLUDING BENZENE DIAMINE DERIVATIVE FOR PREVENTING OR TREATING DEGENERATIVE BRAIN DISEASES

(71) Applicants: UNIST(ULSAN NATIONAL INSTITUTE OF SCIENCE AND TECHNOLOGY), Ulsan (KR); SEOUL NATIONAL UNIVERSITY HOSPITAL, Seoul (KR)

(72) Inventors: Mi Hee Lim, Ulsan (KR); Sang Tae Kim, Seoul (KR); Ho Seong Han, Seoul (KR)

(73) Assignees: UNIST(ULSAN NATIONAL INSTITUTE OF SCIENCE AND TECHNOLOGY), Ulsan (KR); SEOUL NATIONAL UNIVERSITY HOSPITAL, Seoul (KR)

(*) Notice: Subject to any disclaimer, the term of this patent is extended or adjusted under 35 U.S.C. 154(b) by 0 days.

(21) Appl. No.: 15/885,483

(22) Filed: Jan. 31, 2018

(65) Prior Publication Data
US 2019/0092728 A1 Mar. 28, 2019

(30) Foreign Application Priority Data
Sep. 26, 2017 (KR) .................. 10-2017-0124527

(51) Int. Cl.
| | |
|---|---|
| A61K 31/4402 | (2006.01) |
| A61K 31/417 | (2006.01) |
| A61K 31/137 | (2006.01) |
| C07D 213/60 | (2006.01) |
| C07D 233/64 | (2006.01) |
| C07D 213/36 | (2006.01) |
| A61P 25/28 | (2006.01) |
| C07C 323/25 | (2006.01) |
| C07D 213/61 | (2006.01) |
| A61P 25/16 | (2006.01) |

(52) U.S. Cl.
CPC ........... C07D 213/36 (2013.01); A61P 25/16 (2018.01); A61P 25/28 (2018.01); C07C 323/25 (2013.01); C07D 213/61 (2013.01); C07D 233/64 (2013.01)

(58) Field of Classification Search
CPC ............. A61K 31/4402; A61K 31/417; A61K 31/137; C07D 213/60; C07D 233/64
USPC ...... 514/357, 400, 649; 546/329; 548/335.5; 564/306
See application file for complete search history.

(56) References Cited

U.S. PATENT DOCUMENTS

| | | | | |
|---|---|---|---|---|
| 6,593,324 B2 * | 7/2003 | Wurster | ............ | A61K 31/4706 514/233.5 |
| 8,658,650 B2 * | 2/2014 | Conn | ................... | C07D 285/01 514/256 |
| 2016/0283652 A1 * | 9/2016 | Barden | ................. | G16B 15/00 |

OTHER PUBLICATIONS

Fu et al., New Hydroxyquinoline-Based Derivatives as Potent Modulators of Amyloid-.beta. Aggregations, Archiv der Pharmazie, vol. 349, No. 5, pp. 327-341 (Year: 2016).*
Cary et al., Targeting Metal-A.beta. Aggregates with Bifunctional Radioligand [11C]L2-b and a Fluorine-18 Analogue [18F]FL2-b, Medicinal Chemistry Letters, vol. 6, No. 2, pp. 112-116 (Year: 2015).*
Geldenhuys et al., Identification of Multifuntional Small Molecule-Based Reversible Monoamine Oxidase Inhibitors, Med. Chem. Comm., vol. 2, No. 11, pp. 1099-1103 (Year: 2011).*
CAS printout for WO 2010/104324 (Year: 2010).*
Talesa, "Acetylcholinesterase in Alzheimer's Disease," *Mechanisms of Ageing and Development*, 122:1961-1969, 2001.
Pákáski et al., "Interactions between the Amyloid and Cholinergic Mechanisms in Alzheimer's Disease," *Neurochemistry International* 53, pp. 103-111, 2008.
Kása et al., "The Cholinergic System in Alzheimer's Disease," *Progress in Neurobiology*, 52:511-535, 1997.
Jendroska et al., "Amyloid P-Peptide and the Dementia of Parkinson's Disease," *Movement Disorders*, 11(6):647-653, 1996.
Iqbal et al., "Tau in Alzheimer Disease and Related Tauopathies," *Curr. Alzheimer Res.*, 7(8):656-664, 2010.
Beck et al., "Structure-Mechanism-Based Engineering of Chemical Regulators Targeting Distinct Pathological Factors in Alzheimer's Disease," *Nature Communications*, 7(13115):1-13, 2016.
Choi et al., "Design of Small Molecules that Target Metal-Aβ Species and Regulate Metal-Induced Aβ Aggregation and Neurotoxicity," *PNAS*, 107(51):21990-21995, 2010.

* cited by examiner

*Primary Examiner* — Brenda L Coleman
(74) *Attorney, Agent, or Firm* — Klarquist Sparkman, LLP

(57) ABSTRACT

Provided are a compound represented by the following Formula I-1 or I-2, and a composition for preventing or treating dementia or Alzheimer's disease, the composition including the compound and a pharmaceutically acceptable carrier:

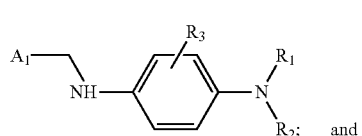

[Formula I-1]

and

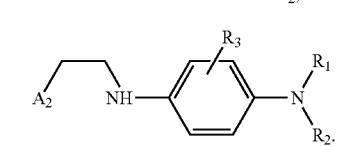

[Formula I-2]

3 Claims, 7 Drawing Sheets

COMPOSITION INCLUDING BENZENE DIAMINE DERIVATIVE FOR PREVENTING OR TREATING DEGENERATIVE BRAIN DISEASES

CROSS-REFERENCE TO RELATED APPLICATION

This application claims the benefit of Korean Patent Application No. 10-2017-0124527, filed on Sep. 26, 2017, in the Korean Intellectual Property Office, the disclosure of which is incorporated herein in its entirety by reference.

BACKGROUND

1. Field

The present disclosure relates to a benzene diamine derivate, or a solvate, stereoisomer, or pharmaceutically acceptable salt thereof, and a composition for preventing or treating degenerative brain diseases including the same as an active ingredient.

2. Description of the Related Art

Degenerative brain diseases are characterized by gradual occurrence of general impairment of mental or physical functions, which is caused by temporary or sustained damage to neurons due to a variety of causes. There are more than 70 diseases reported as degenerative brain diseases. Of them, dementia, Alzheimer's disease, Parkinson's disease, and frontotemporal degeneration are known as representative degenerative brain diseases.

Among these, dementia is one of the diseases with high prevalence, and results from dysfunction of the cerebral cortex, in terms of memory, attention, language, and visual-spatial functioning, and thus patients with dementia suffer from many difficulties in their daily or social lives.

The etiology of dementia has not yet been fully clarified, but Alzheimer's disease (AD) caused by cerebral deposition and aggregation of β-amyloid (Aβ) protein with aging, vascular dementia caused by hardening of the cerebral arteries, alcoholic dementia, etc. are suggested as the causes. The most common type of dementia is Alzheimer's dementia, accounting for 60% or more of cases. Alzheimer's disease has histological features including encephalatrophy, senile plaques, neurofibrillary tangles, granulovacuolar degeneration, and Hirano bodies, which appear in the cerebral cortex and the hippocampus. Aβ is a major component of senile plaques, and it is presumed in turn that deposition of Aβ is the main cause of Alzheimer's disease.

Symptoms of Alzheimer's disease (AD) are closely related to dysfunction of cholinergic synapses as well as cytotoxicity caused by deposition of β-amyloid (Aβ) (P M et el., Interactions between the amyloid and cholinergic mechanisms in Alzheimer's disease. Neurochem Int., 53 (2008): 103-111). Dysfunction of cholinergic synapses is known to contribute to memory and cognitive impairment of Alzheimer's patients. The cholinergic nucleus basalis of Meynert of the basal forebrain as well as the temporal lobe, hippocampus, and amygdala are implicated in memory and cognitive functions, and it is known that the brains of Alzheimer's patients involve neuronal loss of 78% in the temporal lobe, 60% in the hippocampus, and 67% in the nucleus basalis of Meynert. When brain cells are damaged by cytotoxicity, transmission of information, that is, the metabolism of neurotransmitters, is interrupted, which causes memory and cognitive impairment. Many researchers have reported that acetylcholine (ACh) and an enzyme (choline acetyltransferase) responsible for the synthesis of Ach are selectively reduced in Alzheimer's disease. It is also known that deficits in nicotinic and muscarinic acetylcholine receptors and dysfunctions in choline reabsorption and acetylcholine secretion are detected in the brains of patients with Alzheimer's disease, as compared with the brains of normal persons (P M et el., Interactions between the amyloid and cholinergic mechanisms in Alzheimer's disease. Neurochem Int., 53 (2008): 103-111; Talesa V N. Acetylcholinesterase in Alzheimer's disease. Mechanisms of Ageing and Development, 122 (2001): 1961-1969; Kasa P et el., The cholinergic system in Alzheimer's disease. Progress in neurobiology. 52 (1997): 511-535).

In addition to the causes mentioned above, formation of Aβ plaques generates reactive oxygen species (ROS), which causes oxidative stress in nervous tissues, leading to neuronal cell death, and consequently, to Alzheimer's disease.

Most drugs that have been approved as dementia drugs by the FDA are directed to Alzheimer's dementia, and targets of the drugs are limited to acetylcholinesterase. However, inhibitors of this enzyme only function to inhibit the breakdown of ACh, allowing patients to live an ordinary life, but they do not treat the underlying causes of dementia. In addition, there are drug therapies using N-methyl-D-aspartate (NMDA) receptor antagonists. However, since this method is also based on the breakdown of ACh in Alzheimer's patients, it is not a fundamental method of treating Alzheimer's dementia. In other words, there are no drugs that ultimately restore the cause of dementia to a normal state.

SUMMARY

An aspect provides a compound represented by the following Formula I-1 or I-2, or a solvate, stereoisomer, or pharmaceutically acceptable salt thereof:

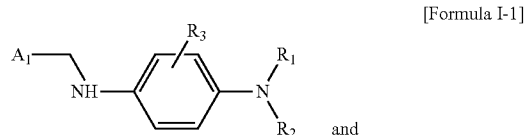

[Formula I-1]

and

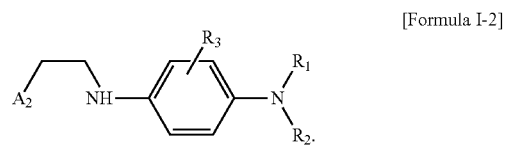

[Formula I-2]

Another aspect provides a composition for preventing or treating degenerative brain diseases, the composition including the compound, or the solvate, stereoisomer, or pharmaceutically acceptable salt thereof, and a pharmaceutically acceptable carrier.

Still another aspect provides a method of preventing or treating neurological disorders, the method including administering the above composition to a subject.

Still another aspect provides a composition for detecting Aβ proteins, the composition including the above composition.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
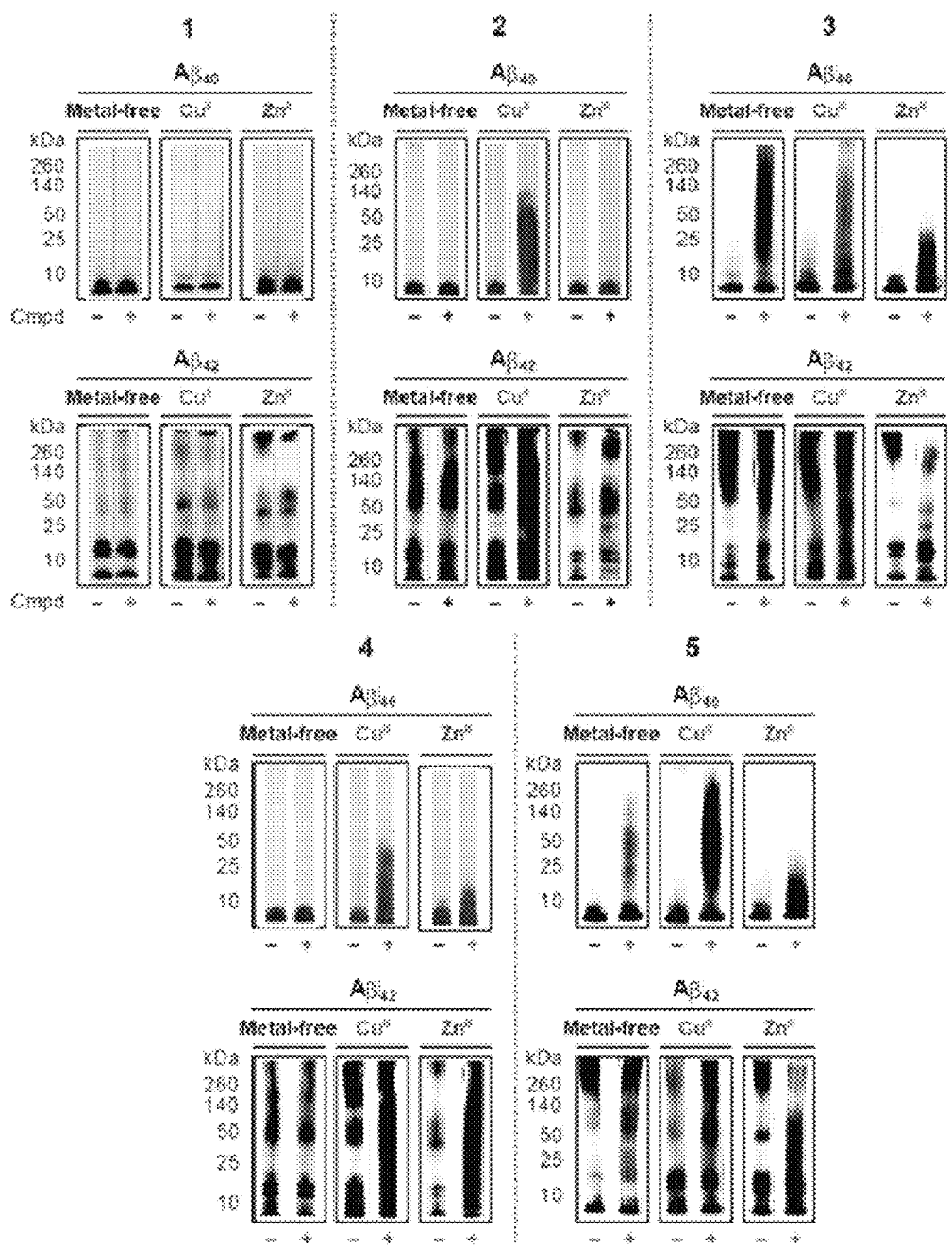
FIG. 1 shows immunoblotting for examining Aβ aggregation-inhibitory effects of Compound 1 to Compound 5 in the presence or absence of metals.

An aspect provides a compound represented by the following Formula I-1 or I-2, or a solvate, stereoisomer, or pharmaceutically acceptable salt thereof:

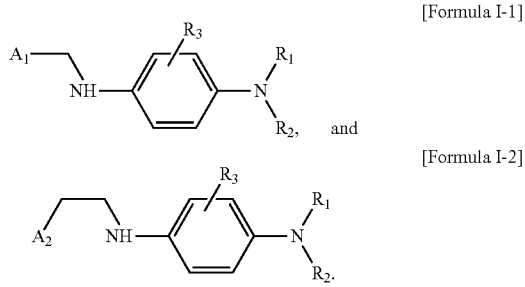

In Formula I-1 or I-2, $R_1$ and $R_2$ are each independently hydrogen or a substituted or unsubstituted $C_1$-$C_6$ alkyl group, or together form a substituted or unsubstituted $C_3$-$C_{10}$ cycloalkyl group or a substituted or unsubstituted $C_2$-$C_{10}$ heterocycloalkyl group;

$R_3$ is selectively and independently hydrogen, a halogen, a hydroxy group, a substituted or unsubstituted amine, a substituted or unsubstituted $C_1$-$C_6$ alkyl group, or a substituted or unsubstituted $C_1$-$C_6$ alkoxy group;

$A_1$ is a substituted or unsubstituted $C_2$-$C_{10}$ heterocycloalkyl group or a substituted or unsubstituted $C_2$-$C_{10}$ heteroaryl group;

$A_1$ is a substituted or unsubstituted $C_2$-$C_{10}$ heterocycloalkyl group, or a substituted or unsubstituted $C_2$-$C_{10}$ heteroaryl group excluding pyridine, in the case where both $R_1$ and $R_2$ are alkyl groups;

$A_2$ is a halogen, a hydroxyl group, —$NH_2$, —$NHR_4$, —$SR_4$, or —$OR_4$;

$R_4$ is hydrogen or a substituted or unsubstituted $C_1$-$C_6$ alkyl group;

a substituent is selected from the group consisting of a halogen, a $C_1$-$C_6$ linear or branched alkyl group, a $C_1$-$C_6$ alkoxy group, a hydroxy group, an amine, a $C_1$-$C_6$ alkylamine group, a nitro group, an amide, a $C_1$-$C_6$ alkylamide, urea, and an acetyl group.

The 'halogen' may be F, Cl, Br, or I.

The 'alkoxy' may be methoxy, ethoxy, n-propoxy, isopropoxy, n-butoxy, isobutoxy, or t-butoxy.

The 'alkyl' refers to linear or branched aliphatic hydrocarbon group having a particular number of carbon atoms, and it may be a methyl, ethyl, n-propyl, isopropyl, butyl, isobutyl, or t-butyl group.

The 'heteroaryl' or 'heterocycloalkyl' group may include one or more heteroatoms selected from B, N, O, S, P(=O), Si, and P, and it may be specifically furyl, thiophenyl, thiazolyl, thiadiazolyl, isothiazolyl, oxadiazolyl, tetrazinyl, furazanyl, pyridyl, azetidinyl, acridinyl, benzodioxolyl, benzodioxanyl, benzofuranyl, carbazolyl, cinnolinyl, dioxolanyl, pyridyl, pteridinyl, purinyl, quinazolinyl, qunioxalinyl, quinolinyl, isoquinolinyl, tetrazolyl, imidazolyl, tetrahydroisoquinolinyl, pyrrolyl, piperonyl, pyrazinyl, pyrimidinyl, pyridazinyl, pyrazolyl, oxazolyl, oxazolinyl, triazolyl, indanyl, isoxazolyl, isoxazolidinyl, decahydroisoquinolyl, benzofuranyl, isobenzofuranyl, benzimidazolyl, benzothiazolyl, benzoisothiazolyl, benzooxazolyl, isoindolyl, indolyl, indazolyl, quinolyl, cinnolinyl, quinazolinyl, quinoxalinyl, carbazolyl, phenanthrinyl, benzodioxolyl, phenylpiperidinyl, tetrahydropuryl, tetrahydropyranyl, piperazinyl, homopiperazinyl, piperidyl, piperidopiperidyl, morpholinyl, thiomorpholinyl, piperidonyl, 2-oxopiperazinyl, 2-oxopiperidinyl, pyrrolidinyl, 2-oxopyrrolidinyl, or oxazolidinyl.

The 'cycloalkyl' may be selected from cyclopropyl, cyclobutyl, cyclopentyl, cyclohexyl, cyclooctyl, cycloheptyl, perhydronaphthyl, adamantly, crosslinked cyclic groups, and spirobicyclic groups.

The 'solvate' refers to the compound of the present disclosure or a salt thereof including a stoichiometric or non-stoichiometric amount of a solvent bound by non-covalent intermolecular forces. Preferred solvents may be solvents which are non-volatile, non-toxic, and suitable for administration to humans.

The 'stereoisomer' refers to those having the same chemical or molecular formula as, but optically or sterically different from, the compounds of the present disclosure or salts thereof, and it may be specifically a diastereoisomer, an enantiomer, a geometrical isomer, or a conformational isomer.

In a specific embodiment, the heterocycloalkyl and heteroaryl groups may be selected from the group consisting of

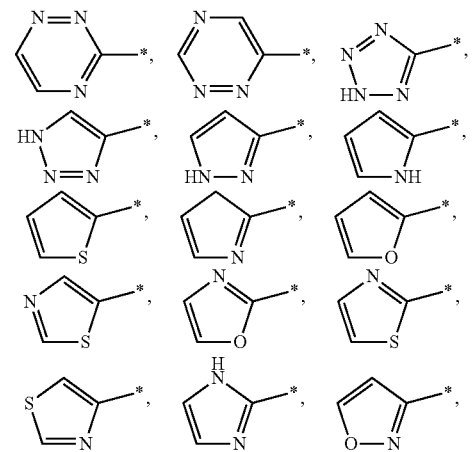

-continued

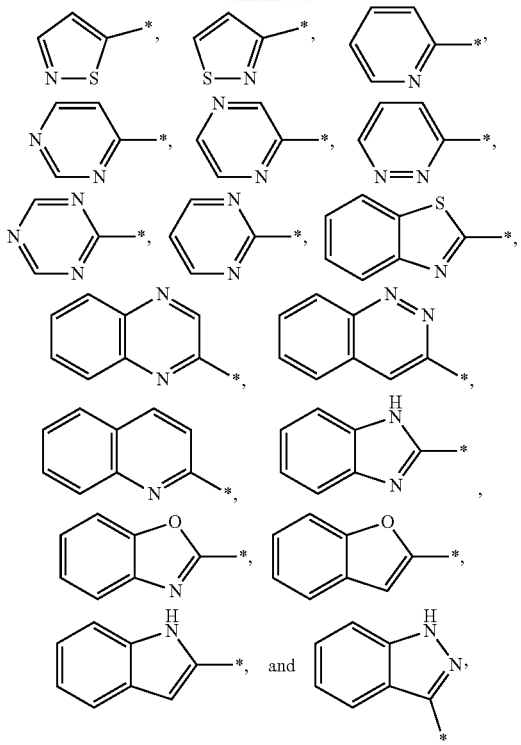

wherein * indicates a binding site with a neighboring atom. The heterocycloalkyl or heteroaryl group may be substituted or unsubstituted.

In a specific embodiment, when both R1 and R2 are an alkyl groups, $A_1$ is a substituted or unsubstituted heterocycloalkyl group excluding pyridine or a substituted or unsubstituted heteroaryl group, and in this regard, the heterocycloalkyl and heteroaryl groups may be selected from the group consisting of -continued

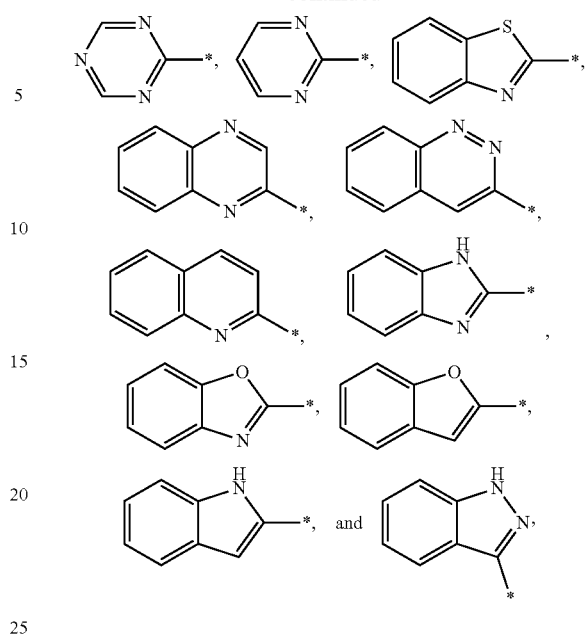

The heterocycloalkyl or heteroaryl group may be substituted or unsubstituted.

In a specific embodiment, the heteroaryl groups may be selected from the group consisting of

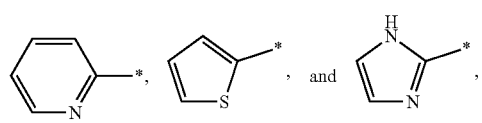

but $A_1$ is a substituted or unsubstituted heteroaryl group excluding pyridine, in the case where both $R_1$ and $R_2$ are alkyl groups, and in this regard, the heteroaryl group may be

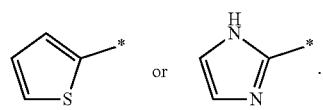 [SMILES: *c1cccs1 ; "or" ; *c1ncc[nH]1 ; "."]

The heteroaryl group may be substituted or unsubstituted.

In a specific embodiment, $A_2$ may be $—SR_4$, $R_4$ may be hydrogen or a substituted or unsubstituted $C_1$-$C_6$ alkyl group.

In a specific embodiment, in $A_2$, $R_4$ may be hydrogen.

In a specific embodiment, the compound represented by Formula I-1 or I-2 may be a compound represented by one of the following Formula II to Formula IV:

[Formula II]

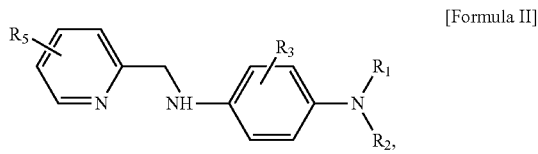

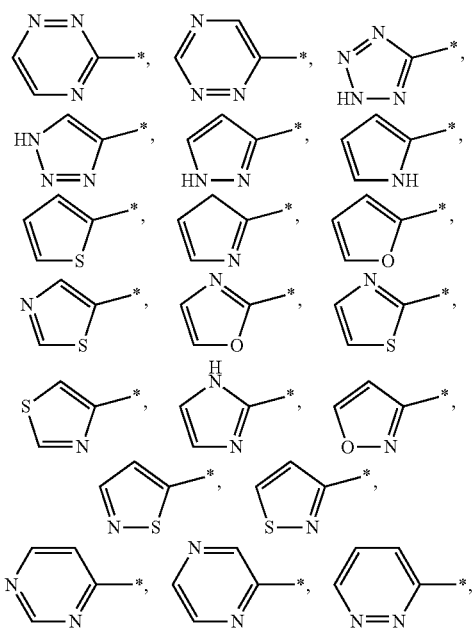

-continued

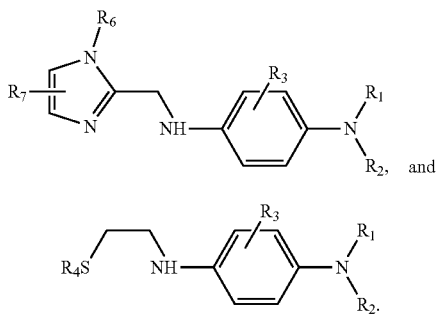

[Formula III]

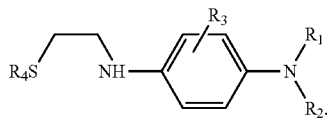

[Formula IV]

In Formula II to Formula IV, $R_1$, $R_2$, $R_3$, and $R_4$ are the same as above;

$R_5$ and $R_7$ are selectively and independently hydrogen, a halogen, a hydroxy group, a substituted or unsubstituted amine, a substituted or unsubstituted $C_1$-$C_6$ alkyl group, or a substituted or unsubstituted $C_1$-$C_6$ alkoxy group $R_6$ is hydrogen or a substituted or unsubstituted $C_1$-$C_6$ alkyl group; and a substituent is selected from the group consisting of a halogen, a $C_1$-$C_6$ linear or branched alkyl group, a $C_1$-$C_6$ alkoxy group, a hydroxy group, an amine, a $C_1$-$C_6$ alkylamine group, a nitro group, an amide, a $C_1$-$C_6$ alkylamide, urea, and an acetyl group.

In a specific embodiment, $R_5$ may be hydrogen or a halogen.

In a specific embodiment, $R_5$ may be hydrogen or fluorine.

In a specific embodiment, in Formula II, $R_1$ and $R_2$ may be each hydrogen.

In a specific embodiment, in Formula III and Formula IV, $R_1$ and $R_2$ may be each independently a substituted or unsubstituted $C_1$-$C_6$ alkyl group.

In a specific embodiment, in Formula III and Formula IV, $R_1$ and $R_2$ may be each a methyl group.

In a specific embodiment, the compound represented by Formula I-1 or I-2 may be a compound represented by one of the following Formulae:

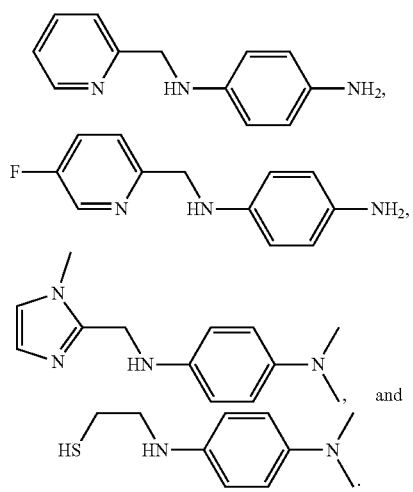

Another aspect provides a composition for preventing or treating degenerative brain diseases, the composition including any one compound of the above-described compounds, or a solvate, stereoisomer, or pharmaceutically acceptable salt thereof.

The 'pharmaceutically acceptable salt' refers to a salt which has effective action relatively non-toxic and harmless to patients, and whose side effects do not degrade the beneficial efficacy of the compound in the composition of the present disclosure. The pharmaceutically acceptable salt refers to any organic or inorganic addition salt of the compound. The salt may use an inorganic acid and an organic acid as a free acid. The inorganic acid may be hydrochloric acid, bromic acid, nitric acid, sulfuric acid, perchloric acid, phosphoric acid, etc. The organic acid may be citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, malonic acid, etc. In addition, these salts include alkali metal salts (sodium salts, potassium salts, etc.) and alkaline earth metal salts (calcium salts, magnesium salts, etc.). For example, the acid addition salt may include acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc., and among them, hydrochloride or trifluoroacetate may be used.

The compound of the present disclosure has effects of inhibiting Aβ aggregation in the absence or presence of various Aβ proteins and metals and of reducing oxidative stress on neuronal cells by reactive oxygen species. A correlation of Aβ protein with dementia and Alzheimer's disease is very well-known, and high Aβ deposition or aggregation is also observed in Parkinson's disease, which has been reported to be closely associated with Parkinson's disease dementia that often occurs with Parkinson's disease (Mov Disord. November; 11(6) (1996): 647-53, etc.). It was also reported that excessive Aβ may promote hyperphosphorylation of tau protein, which is associated with formation of neurofibrillary tangles in frontotemporal degeneration (Curr Alzheimer Res. 2010 December; 7(8): 656-664).

Therefore, in a specific embodiment, the degenerative brain disease may be specifically dementia, Alzheimer's disease, Parkinson's disease, or frontotemporal degeneration (or pick's disease). The dementia may be cerebrovascular dementia, Alzheimer's dementia, Parkinson's dementia, diabetic dementia, senile dementia, or Lewy body dementia.

Still another aspect provides a health functional food for preventing or alleviating degenerative brain diseases, the health functional food including any one compound of the above-described compounds, a solvate, stereoisomer, or health functional food-acceptable salt thereof.

When the compound of the present disclosure may be included in the health functional food, the compound may be added as it is or used together with other health functional foods or health functional food ingredients according to a common method. A mixing amount of the active ingredient may be determined according to the purpose of use. Generally, the active ingredient constituting the composition according to the present disclosure may be included in an amount of 0.01% by weight to 15% by weight, preferably 0.2% by weight to 10% by weight, based on the total weight of the food. When prepared as a drink, the compound may be included in an amount of 0.1 g to 30 g, preferably 0.2 g to 5 g, based on 100 ml, and the entire drink may be composed of natural ingredients. However, for long-term intake for health control and hygiene, the amount may be below the above range. Since the active ingredient does not have any safety problems, it may be used in a larger amount than the above range.

The health functional food composition according to the present disclosure may be prepared as a common health functional food formulation known in the art. The health functional food may be prepared as, for example, a powder, a granule, a tablet, a pill, a capsule, a suspension, an emulsion, a syrup, an infusion, a liquid, an extract, a vitamin complex, a gum, a tea, a jelly, a beverage, etc., and preferably, as a beverage. As a food-acceptable carrier or additive, any carrier or additive which is known in the art to be applicable in the preparation of a desired formulation may be used. The health functional food may include nutrients, vitamins, electrolytes, flavors, sweeteners (e.g., stevia, rebaudioside A, glycyrrhizin, thaumatin, saccharin, aspartame, etc.), extenders (e.g., cheese, chocolate, etc.), colorants, pectic and salts thereof, alginic acid and salts thereof, organic acids, sugars (e.g., glucose, fructose, maltose, sucrose, dextrin, cyclodextrin, xylitol, sorbitol, erythritol, etc.), protective colloidal viscofiers, pH regulators, stabilizers, antiseptics, glycerin, alcohols, carbonators used in carbonated drinks, etc. according to the purpose or preference. In addition, the health functional food may include pulp for preparing a natural fruit juice, a fruit juice beverage, or a vegetable beverage. Further, the health functional food composition may further include a food additive. The suitability of the "food additives" may be determined by the specification and standard of the concerned item in accordance with the General Provisions and General Test Methods of the Korea Food Additives Code authorized by the Korea Food and Drug Administration, unless otherwise specified.

Still another aspect provides a method of preventing or treating degenerative brain diseases, the method including administering the above-described compound, or a solvate, stereoisomer, or pharmaceutically acceptable salt thereof to a subject in need thereof.

The subject may be a mammal, for example, a human, a cow, a horse, a pig, a dog, a sheep, a goat, or a cat, and the mammal may be a human. An administration dose of the compound of the present disclosure effective for the human body may vary depending on age, body weight, and sex of a patient, administration mode, health conditions, and disease severity. The pharmaceutical composition including the compound of the present disclosure may be safely used for a long period of time for prophylactic purposes, because it rarely has toxicity and side-effects.

The administration may be performed by various formulations for oral administration or parenteral administration such as intravenous, intraperitoneal, transdermal, intradermal, subcutaneous, epithelial, rectal, inhalation, nasal, sublingual, or intramuscular administration. Formulations may be prepared by using a diluent or an excipient such as a filler, an extender, a binder, a wetting agent, a disintegrant, a surfactant, etc., which is commonly used.

A solid formulation for oral administration may include tablets, pills, powder, granules, fine granules, capsules, suspensions, oral solutions, rapidly dispersing tablets, syrups, chewable tablets, troches, etc. Such solid formulations may be prepared by mixing one or more of the compound of the present disclosure with at least one excipient, for example, starch, calcium carbonate, sucrose, lactose, gelatin, etc. In addition to simple excipients, lubricants such as magnesium stearate or talc may also be used. As a liquid formulation for oral administration, suspensions, liquids for internal use, emulsions, syrups, etc. may be used. In addition to simple diluents that are frequently used, such as water or liquid paraffin, various excipients, for example, wetting agents, sweeteners, fragrances, preservatives, etc. may be included.

Formulations for parenteral administration may include sterilized aqueous solutions, injectable formulations, non-aqueous solvents, suspensions, emulsions, lyophilized formulations, aerosols, nasal administration, emulsions, suppositories, etc. For the non-aqueous solvent or suspension, propylene glycol, polyethylene glycol, vegetable oils such as olive oil, or injectable esters such as ethyloleate may be used. For a base material of suppositories, witepsol, macrogol, tween 61, cacao butter, laurin butter, glycerol, gelatin, etc. may be used.

External preparations to be applied to the skin may be applied in a form of a patch, a band, an emulsion, an ointment, a pack, a gel, a cream, a lotion, a liquid, or a powder. As a cosmetic, a skin softener, a nutrient lotion, a massage cream, a nutrient cream, a moisturizing cream, a functional cream, a mist, a pack, a gel, or a skin adhesive-type formulation may be applied. Therefore, to be used for external application, ingredients commonly used in external preparations such as cosmetics or drugs, for example, an aqueous ingredient, an oily ingredient, a powdery ingredient, alcohols, a moisturizing agent, a thickener, an UV absorbing agent, a whitening agent, a preservative, an antioxidant, a surfactant, a flavoring agent, a colorant agent, several skin nutrition agents, etc. may be properly blended with the composition, as needed. The external preparations may be properly blended with a sequestering agent, such as disodium edetate, trisodium edetate, sodium citrate, sodium polyphosphate, sodium metaphosphate, gluconic acid, etc., a drug, such as caffeine, tannin, verapamil, licorice extract, glabridin, a hot water extract of fruit of carlin, various crude drugs, tocopherol acetate, glycyrrhizic acid, tranexamic acid and their derivatives or salts, vitamin C, magnesium phosphate ascorbate, glucoside ascorbate, albutin, kojic acid, and sugars such as glucose, fructose, trehalose, etc.

Still another aspect provides a composition for detecting Aβ proteins, the composition including the compound of the present disclosure, a solvate, stereoisomer, or salt thereof; and one or more probes.

Since the benzene diamine derivative has a properly positioned electron donating atom, such as a nitrogen atom, within the compound, it is able to bind with Aβ protein (Nature communications 7, 13115(2016), PNAS (2010); 107; 51). Such a property inhibits formation of Aβ aggregates or plaques. Therefore, the compound of the present disclosure is bound with a probe (e.g., a fluorescent probe), and the binding property of the compound with Aβ protein may be employed in the composition for detecting Aβ protein.

In a specific embodiment, the Aβ protein may be Aβ40 or Aβ42.

In a specific embodiment, the Aβ protein may be metal-free Aβ, Cu(II)-Aβ, Zn(II)-Aβ, or a combination thereof.

Still another aspect provides a method of diagnosing degenerative brain diseases, the method including contacting the composition for detecting Aβ protein with a body fluid obtained from a subject.

The body fluid may be blood, plasma, serum, sweat, saliva, urine, spinal fluid, but is not limited thereto.

The method of diagnosing degenerative brain diseases may further include visualizing a complex of the composition for detecting Aβ protein and Aβ protein in order to detect the complex. The visualizing may be measuring absorbance by irradiating light with a predetermined wavelength, such as UV, to the probe of the composition for detecting Aβ protein, or by measuring fluorescence excitation.

Among the terms or elements mentioned in the composition for detecting Aβ protein and the method of diagnosing degenerative brain diseases, those mentioned in the description of the claimed compound or composition for treating degenerative brain diseases including the compound are interpreted as being the same as those mentioned in the claimed composition for detecting Aβ protein and method of diagnosing degenerative brain diseases.

A compound represented by the following Formula I-1 or I-2, or a solvate, stereoisomer, or pharmaceutically acceptable salt thereof according to an aspect may be used for the prevention or treatment of degenerative brain diseases by controlling Alzheimer risk factors, that is, metal-free Aβ, metal-Aβ, and reactive oxygen species.

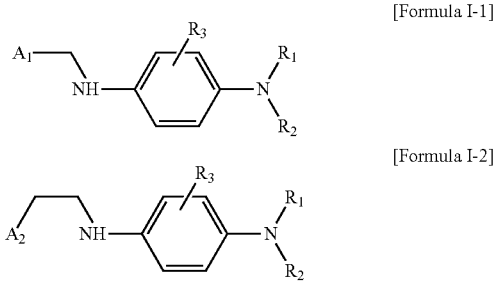

[Formula I-1]

[Formula I-2]

A composition including the compound, or the solvate, stereoisomer, or pharmaceutically acceptable salt thereof, and a pharmaceutically acceptable carrier according to another aspect may be used for the treatment of a degenerative brain disease of a subject, specifically, dementia, Alzheimer' disease, Parkinson's disease, or frontotemporal degeneration.

A composition for detecting Aβ protein including the compound, or the solvate, stereoisomer, or salt thereof; and one or more probes according to still another aspect may be used for the diagnosis of a degenerative brain disease, specifically, dementia, Alzheimer' disease, Parkinson's disease, or frontotemporal degeneration.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. Expressions such as "at least one of", when preceding a list of elements, modify the entire list of elements and do not modify the individual elements of the list.

Hereinafter, the present invention will be described in more detail with reference to Examples. However, these Examples are for illustrative purposes only, and the invention is not intended to be limited by these Examples.

1. Example 1: Synthesis of Benzene Diamine Derivatives

Benzene diamine derivatives were synthesized as follows.

1-1. Synthesis of $N^1$-(pyridin-2-ylmethyl)benzene-1,4-diamine (Compound 2)

(1) Step 1

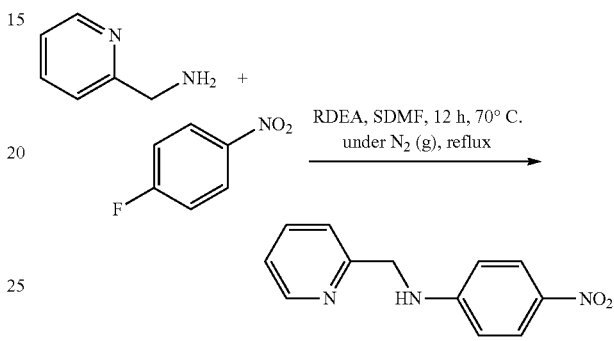

Under a nitrogen atmosphere, 1-fluoro-4-nitrobenzene (231 µl, 2.2 mmol), N,N-diisopropylethylamine (836 µl, 4.8 mmol), and DMF (25 mL) were put in a well-dried flask equipped with a reflux condenser and a magnetic stirrer, and then 2-(aminoethyl)pyridine (247 µl, 2.4 mmol) was added thereto at room temperature, and this mixture was heated at 70° C. 12 hours later, water (75 mL) was added to a resulting brown solution, and extracted with EtOAc (3×75 mL). An extracted organic solution was washed with water (2×75 mL) and brine (75 mL). Thereafter, $MgSO_4$ was added thereto, and filtration was performed, and then a filtrate was concentrated. This concentrated solution was purified by silica column chromatography (EtOAc in n-hexane from 25% to 100%) to obtain a yellow solid compound (0.29 g, yield: 58%). [TLC condition (EtOAc:n-hexane=50:50 (v/v)): Rf=0.25].

(2) Step 2

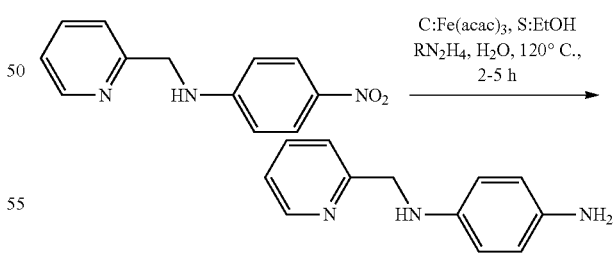

The compound (0.52 g, 2.3 mmol) obtained in Step 1, tris(acetylacetonato)iron (III) (0.024 g, 3 mol %), and ethanol (20 mL) were put in a well-dried flask equipped with a reflux condenser and a magnetic stirrer, and then mixed with hydrazine hydrate (581 µl, 11 mmol). This mixture was heated under reflux for 2 hours at 120° C. 2 hours later, when the reactants remained, 4 equivalents of hydrazine hydrate was further added every hour. Resulting brown oil was concentrated and purified by silica column chromatography

[EtOAc:Et₃N(99%:1%) in EtOAc (100%); TLC condition: (EtOAc:Et₃N=99:1 (v/v)), Rf=0.20]. The purified compound was dissolved in a small amount of MeOH, and excess 5 M HCl was added thereto to produce a compound in the form of a salt. A product was concentrated under vacuum and then washed with Et₂O (3×5 mL). This resulting compound was dissolved in water (20 mL) to produce an aqueous layer, which was washed with Et₂O (3×20 mL), and concentrated. Water was removed under vacuum and recrystallization was performed with MeOH and Et₂O. A product was a light yellow solid (0.45 g. yield: 85%).

1-2. Synthesis of $N^1$-((5-fluoropyridin-2-yl)methyl)benzene-1,4-diamine (Compound 3)

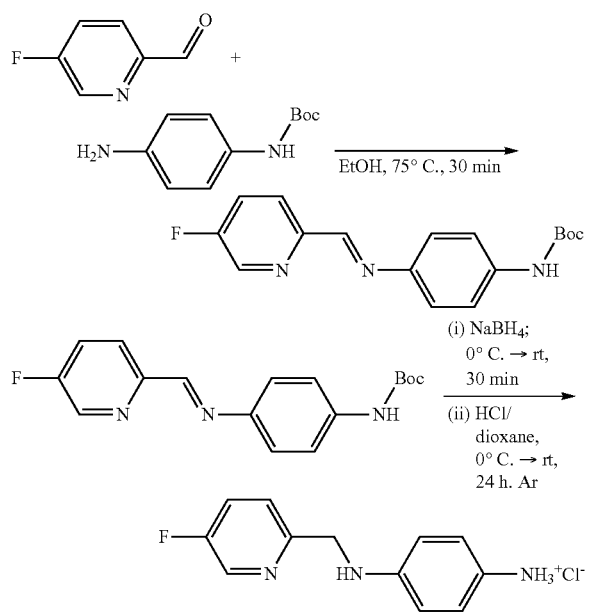

5-fluoropyridine-2-carboxaldehyde (20 mg, 0.152 mmol) was added to an ethanol solution (EtOH; 1.5 mL) containing N-(tert-butoxycarbonyl)-1,4-phenylenediamine (33.3 mg, 0.152 mmol). This reaction mixture was stirred at 75° C. for 24 hours. The solvent was concentrated under vacuum without other purification procedure to obtain a yellow solid product (50.4 mg, 0.152 mmol). Sodium borohydride (NaBH₄, 34.5 mg, 0.911 mmol) was added to methanol (2 mL, cooled to 0° C.) to obtain a solution of an imine product. This solution was stirred at 0° C. for 5 minutes. After 30 minutes at room temperature, this reaction was quenched with H₂O, and extracted with ethyl acetate (EtOAc, 3×). This mixed organic phase was washed with brine (1×) and dried over anhydrous magnesium sulfate (MgSO₄). This crude compound was purified by column chromatography (SiO₂, EtOAc: hexanes=1:6 to 1:2) to obtain a white solid product (33.9 mg, 0.107 mmol, 70.4%). An HCl/dioxane (4 mL, 4.0 M) solution was cooled at 0° C. under Ar (g) in a round-bottom flask equipped with a magnetic stirrer. A Boc-protected compound was added, and then the reactant was stirred at room temperature. 24 hours later, the solvent was concentrated under vacuum. Residues were washed with diethyl ether (Et₂O) and filtered and collected to obtain a yellow solid product (10.2 mg, 0.04 mmol, 37.6%). ¹H NMR [400 MHz, DMSO-d6, δ (ppm)]: 10.0 (3H, s), 8.63 (1H, d, J=3.2 Hz), 7.83 (1H, td, J=2.8 Hz, J=12.4), 7.55 (1H, m), 7.14 (2H, d, J=8.8 Hz), 6.77 (2H, d, J=8.8 Hz), 4.47 (6H, s). ¹³C NMR [100 MHz, DMSO-d6, δ (ppm)]: 160.1, 157.6, 154.7, 146.5, 136.4, 126.01, 124.2, 122.1, 114.7, 48.2. ESI-MS (m/z): [M+H]⁺ Calcd. for $C_{12}H_{13}FN_3^+$, 218.1; found, 218.0.

1-3. Synthesis of $N^1,N^1$-dimethyl-$N^4$-((1-methyl-1H-imidazol-2-yl)methyl)benzene-1,4-diamine (Compound 4)

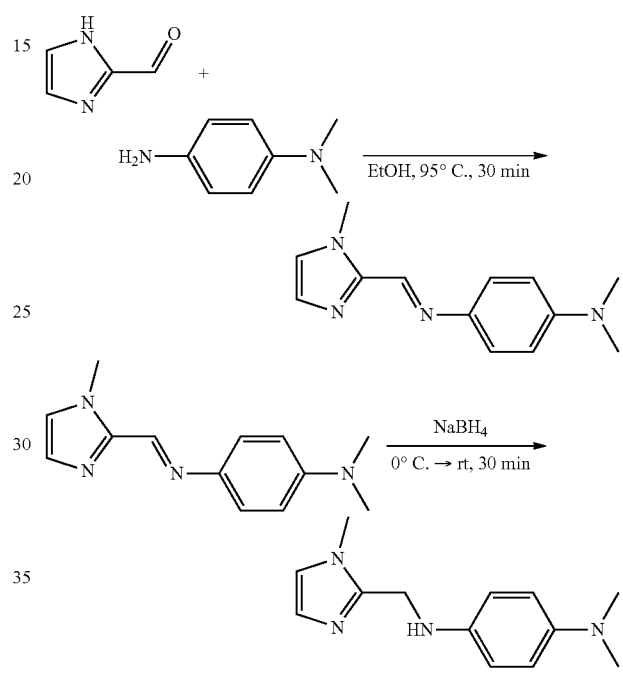

1H-imidazole-2-carbaldehyde (84.7 μl, 0.88 mmol) and N/N-dimethylbenzene-1,4-diamine (115 μl, 0.88 mmol) were put in a test tube containing EtOH (1.2 mL) with a magnetic stirrer. This reaction mixture was stirred at 95° C. under N₂ (g) for 30 minutes. The solution was cooled to 0° C., and then NaBH₄ (222 mg, 5.87 mmol) dissolved in MeOH (3 mL, cooled to 0° C.) was directly added to the imine product solution. This reaction mixture was stirred at room temperature for 30 minutes. The reaction was quenched with H₂O, and extracted with Et₂O (3×). A product (brown solid; 89.1 mg, 0.39 mmol, 44%) was obtained from Et₂O and hexane by recrystallization. ¹H NMR [400 MHz, DMSO-d6, δ (ppm)]: 8.51 (1H, s), 7.36 (1H, s), 7.27 (2H, d, J=8.8 Hz), 7.10 (1H, s), 6.77 (2H, d, J=8.8 Hz), 4.05 (3H, s), 2.93 (6H, s). ¹³C NMR [100 MHz, DMSO-d6, δ (ppm)]: 146.2, 143.6, 141.3, 126.4, 122.1, 115.8, 114.1, 42.2, 41.3, 32.8. ESI-MS (m/z): [M+H]⁺ Calcd. for $C_{13}H_{19}N_4^+$, 231.2; found, 231.3.

1-4. Synthesis of 2-((4-(dimethylamino)phenyl)amino)ethane-1-thiol (Compound 5)

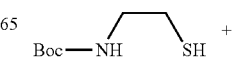

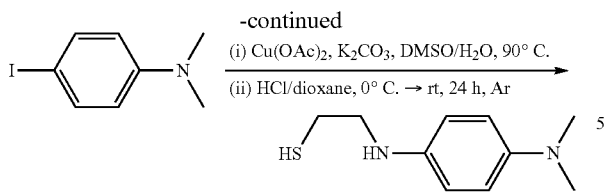

4-iodo-N,N-dimethylaniline (490 mg, 2.0 mmol), 2-(Boc-amino)ethanethiol (680 µl, 4.0 mmol), copper acetate dihydrate [Cu(OAc)$_2$.2H$_2$O; 40 mg, 0.2 mmol], and potassium carbonate (K$_2$CO$_3$; 1.1 g, 8.0 mmol) were put in a test tube with a magnetic stirrer containing DMSO/H$_2$O (3 mL/1 mL). After being flushed with Ar (g), the mixture was stirred in an oil bath preheated at 90° C. for 24 hours. This solution was cooled at room temperature, and then the reaction was quenched with EtOAc. The reaction solution was washed with H$_2$O (3×), and brine (1×). The organic layer was dried over MgSO$_4$, and concentrated under vacuum. A crude product was purified by column chromatography (SiO$_2$; EtOAc:hexane=1:10) to obtain a product (white solid; 210 mg, 0.71 mmol, 34%). tert-butyl 2-(4-(dimethylamino)phenylthio)ethyl carbamate (400 mg, 1.4 mmol) was added under Ar (g) at 0° C. to a HCl/dioxane (4.0 M, 10 mL) solution. This reaction mixture was stirred at room temperature for 24 hours. The solvent was removed under vacuum, and residues were washed with diethyl ether (Et$_2$O). A sticky compound was alkalized with 1 N NaOH (aq) and extracted with EtOAc (3×). The combined organic layer was washed with brine (1×), and dried over anhydrous MgSO$_4$, and concentrated under vacuum. A crude compound was purified by column chromatography (SiO$_2$; CH$_2$Cl$_2$:CH$_3$OH=7:1). A product (white powder; 50 mg, 0.25 mmol, 18%) was obtained by adding Et$_2$O to a yellow liquid product. $^1$H NMR [400 MHz, CD3OD, δ (ppm)]: 7.35 (2H, m), 6.72 (2H, d, J=8.8 Hz), 2.94 (10H, m), 1.90 (2H, s). $^{13}$C NMR [100 MHz, CD3OD, δ (ppm)]: 152.2, 136.0, 119.2, 114.2, 40.6. 39.8, 35.5. HRMS (m/z): [M+H]$^+$ Calcd. for C$_{10}$H$_{17}$N$_2$S$^+$, 197.1107; found, 197.1103.

Compounds 2 to 5 thus obtained were freeze-dried to obtain dry powders. The obtained Compounds 2 to 5 were extracted simply with an aqueous solution and dried to obtain dry powders.

A variety of benzene diamine derivatives of the present disclosure may be prepared by a method well known to those skilled in the art, without being limited to the above-described Compounds 2 to 5.

2. Example 2: Examination of Inhibitory Effect on Aβ Aggregation

It was examined whether the benzene diamine derivatives of the present disclosure have inhibitory effects on Aβ aggregation. Aβ has two isoforms, and therefore, effects on Aβ40 and Aβ42 were examined, respectively. When metals are involved in protein folding, the probability of abnormal folding is high. In this case, the probability of Aβ aggregate formation is further increased. Therefore, it was examined whether each compound in the presence or absence of metal also exhibited inhibitory effects on Aβ aggregation.

2-1. Molecular Analysis of Aβ Aggregation-Inhibitory Effect

In order to perform molecular analysis of Aβ aggregation-inhibitory effects of the benzene diamine derivatives of the present disclosure, gel electrophoresis and Western blotting were performed by using anti-Aβ antibody (6E10). As a control group, compound 1

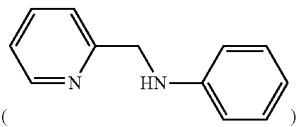 [SMILES: c1ccc(NCc2ccccn2)cc1]

was used.

In detail, each sample (10 µl) was separated on a 10-20% Tris-tricine gel (Invitrogen, Grand Island, N.Y., USA). After separation, the proteins were transferred onto a nitrocellulose membrane and blocked with bovine serum albumin (BSA, 3% w/v, Sigma-Aldrich, St Louis, Mo., USA) in Tris-buffered saline (TBS) containing 0.1% Tween-20 (TBS-T) at room temperature for 2 hours or at 4° C. overnight. The membrane was incubated in a 2% BSA (w/v in TBS-T) solution, together with anti-Aβ antibody (6E10, 1:2,000, Covance, Princeton, N.J., USA), at room temperature for 4 hours or at 4° C. overnight. The membrane was washed with TBS-T (3×, 10 min), and a secondary mouse antibody (1:5,000 in 2% BSA w/v in TBS-T; Cayman Chemical Company, Ann Arbor, Mich., USA) was added thereto, followed by incubation at room temperature for 1 hour. Thermo Scientific SuperSignal West Pico Chemiluminescent Substrate (Thermo Scientific, Rockford, Ill., USA), Biosesang ECL Plus kit (Biosesang, Gyeonggi-do, Republic of Korea), or homemade ECL kit53 were used for visualization, and ChemiDoc MP Imaging System (Bio-Rad, Hercules, Calif., USA) was used for detection.

As a result, Compound 1 did not show inhibitory effect on Aβ aggregation under any conditions. In contrast, Compound 2 showed very excellent Cu(II)-Aβ-inhibitory effect on two kinds of Aβ. Compound 3 and Compound 5 showed inhibitory effect on both two kinds of Aβ, irrespective of the kind and presence of metals. Particularly, Compound 4 showed inhibitory effect on Aβ with metals. Accordingly, it can be seen that although there is a slight tendency difference, the benzene diamine derivatives of the present disclosure have inhibitory effects on Aβ aggregation (FIG. 1).

2-2. Morphological Analysis of Aβ Aggregation-Inhibitory Effect

Aβ aggregation-inhibitory effect of the benzene diamine derivative (Compound 2) of the present disclosure was examined by using an electron microscope to confirm a morphological change.

In detail, a sample for TEM was prepared according to a method previously known, and Glow-discharged grids (Formvar/Carbon 300-mesh, Electron Microscopy Sciences, Hatfield, Pa., USA) were treated with an Aβ sample (25 µM, 5 µl), followed by incubation at room temperature for 2 hours. The remaining sample was removed by using a filter paper, and the grids were washed with ddH$_2$O twice. Each grid was incubated with uranyl acetate (1%, ddH$_2$O, 5 µl) for 1 minute, and blotted off, and then dried at room temperature for 15 minutes. An image of each sample was obtained by a JEOL JEM-2100 transmission electron microscope (UNIST Central Research Facilities, Ulsan National Institute of Science and Technology, Ulsan, Republic of Korea).

Figure 2:
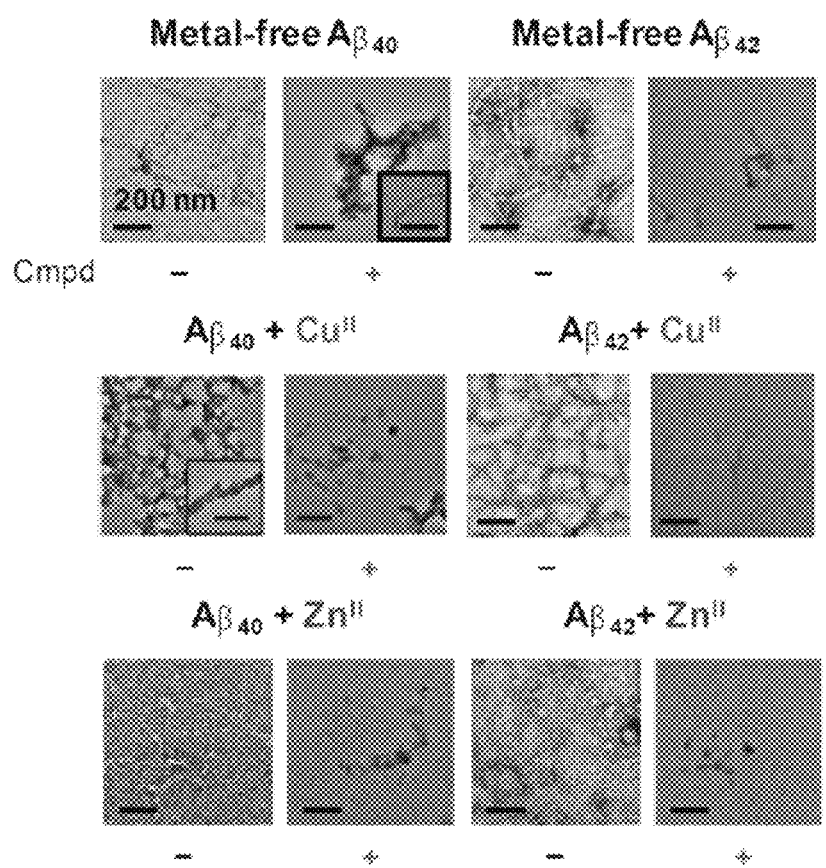
FIG. 2 shows an image of Aβ aggregation-inhibitory effects of Compound 2 in the presence or absence of metals.

As a result, the images showed that the benzene diamine derivative has the inhibitory effect on Aβ aggregation (FIG. 2).

3. Example 3: Examination of Antioxidant Effect

It was examined whether the benzene diamine derivatives of the present disclosure have an antioxidant effect. It is known that reactive oxygen species induces oxidative stress in neuronal cells to cause neuronal cell death and causes protein misfolding to induce formation of Aβ aggregates. Therefore, compounds having antioxidant effects may be candidates for preventing or treating dementia.

Free organic radical-scavenging activity of the compound was determined according to a protocol of Cayman Chemical Company (Ann Arbor, Mich., USA) with slight modifications. For antioxidant analysis using a cell lysate, cells were seeded in a 6-well plate, and cultured until they reached 80-90% confluence. A cell lysate was prepared according to a known method, washed with a cold phosphate buffer solution (PBS; pH 7.4, GIBCO), and then harvested. Cell pellet was produced by centrifugation (2,000 g, 4° C., 10 min). This pellet was sonicated (5 sec pulse, 20 sec interval, three times) in 2 ml of cold assay buffer S13 (5 mM potassium phosphate, pH 7.4; 0.9% NaCl; 0.1% glucose) on ice. A cell lysate was centrifuged at 4° C. for 10 minutes at 5,000 g. A supernatant was removed, and left on ice until use. To the cell lysate supernatant (10 μl), the compound, metmyoglobin, ABTS (2,2'-azino-bis-3-ethylbenzothiazoline-6-sulfonic acid), and hydrogen peroxide were sequentially added. The mixture was incubated on a shaker at room temperature for 5 minutes, and absorbance at 750 nm was measured. The compound at a final concentration of 45, 90, 135, 180, 225, or 330 μM and Trolox (6-hydroxy-2,5,7,8-tetramethyl-chroman-2-carboxylic acid, dissolved in EtOH) were used. Antioxidant activity was calculated according to the measured absorbance [% inhibition=100×(A0−A)/A0, A0 represents absorbance of the supernant of the cell lysate]. Each measurement was repeated in triplicate.

Figure 3:
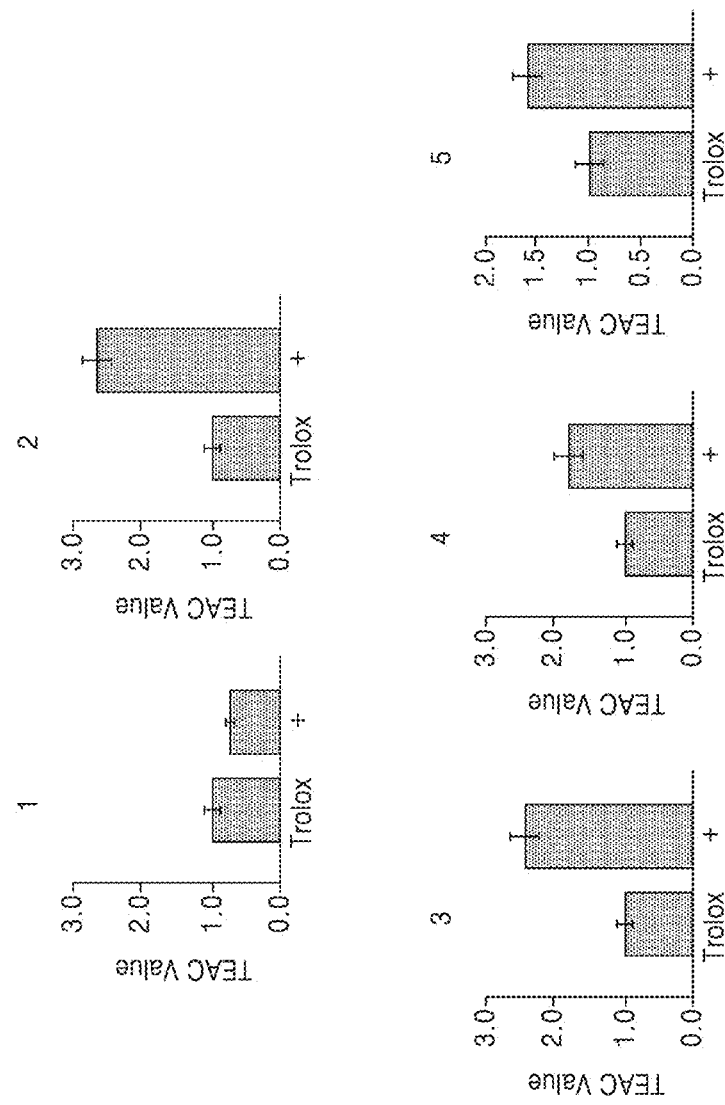
FIG. 3 shows antioxidant effects of Compound 1 to Compound 5.

As a result, all of Compounds 2 to 5, excluding Compound 1, inhibited a free radical which is one of reactive oxygen species, and they showed remarkable effects, as compared with Trolox (vitamin E analogue) which is known as an antioxidant material (FIG. 3). Therefore, it can be seen that Compounds 2 to 5 sufficiently counterbalance oxidative stress in neuronal cells to prevent neuronal cell death, and furthermore, they have excellent prophylactic or therapeutic effects on dementia or Alzheimer's disease.

Results of Examples 2 and 3 are summarized in the following Table 1.

TABLE 1

| Compound | Metal-free Aβ | Cu(II)-Aβ | Zn(II)-Aβ | Reactive oxygen species |
|---|---|---|---|---|
| 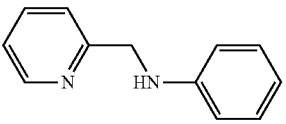 [SMILES: c1ccc(NCc2ccccn2)cc1] Compound 1 | — | — | — | No effect |
| 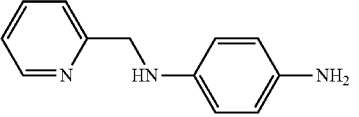 Compound 2 | — | ○ | — | ○ (better effect than TEAC) |
| 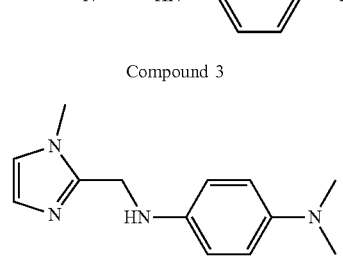 Compound 3 | ○ | ○ | ○ | ○ |
| 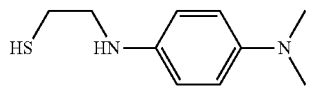 Compound 4 | — | ○ | ○ | ○ |
| 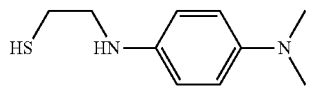 Compound 5 | ○ | ○ | ○ | ○ |

4. Example 4: Examination of Cytotoxicity-Inhibitory Effect

It was examined whether the benzene diamine derivatives of the present disclosure have cytotoxicity-inhibitory effect. Aβ aggregation and reactive oxygen species may cause cytotoxicity in neuronal cells, resulting in neuronal cell death. Therefore, it was confirmed whether the benzene diamine derivatives of the present disclosure may substantially inhibit cytotoxicity beyond the Aβ aggregation inhibitory and antioxidant effects, thereby increasing cell viability.

In detail, human neuroblastoma cell line SK-N-BE(2)-M17 (M17) (ATCC, Manassa, Va., USA) was cultured in a 1:1 minimum essential medium (MEM; GIBCO, Grand Island, N.Y., USA), Ham's F12K Kaighn's Modification Media (F12K; GIBCO) supplemented with 10% (v/v) fetal bovine serum (FBS; Atlanta Biologicals, Flowery Branch, Ga., USA), 100 U/mL penicillin (GIBCO), and 100 mg/mL streptomycin (GIBCO). M17 cells were seeded in a 96-well plate (150,000 in 100 µl per well), and treated with various concentrations of the compound (0-50 µM, 1% v/v DMSO) in the presence or absence of $CuCl_2$ or $ZnCl_2$ (a metal/ligand ratio of 1:1 or 1:2), and in the presence or absence of Aβ 40 (Aβ:metal:compound=10:10:20 µM). After incubation at 37° C. for 24 hours, 25 µl of MTT (3-(4,5-dimethylthiazol-2-yl)-2,5-diphenyltetrazolium bromide) (5 mg/mL in PBS, pH 7.4) (GIBCO) was added to each well, and each plate was incubated at 37° C. for 4 hours. Formazan produced from cells was dissolved in a solution containing N,N-dimethylformamide (DMF, 50% v/v aq) and sodium dodecyl sulfate (SDS, 20% w/v), and incubated at room temperature overnight. Absorbance at 600 nm was measured by using a microplate reader.

Figure 4:
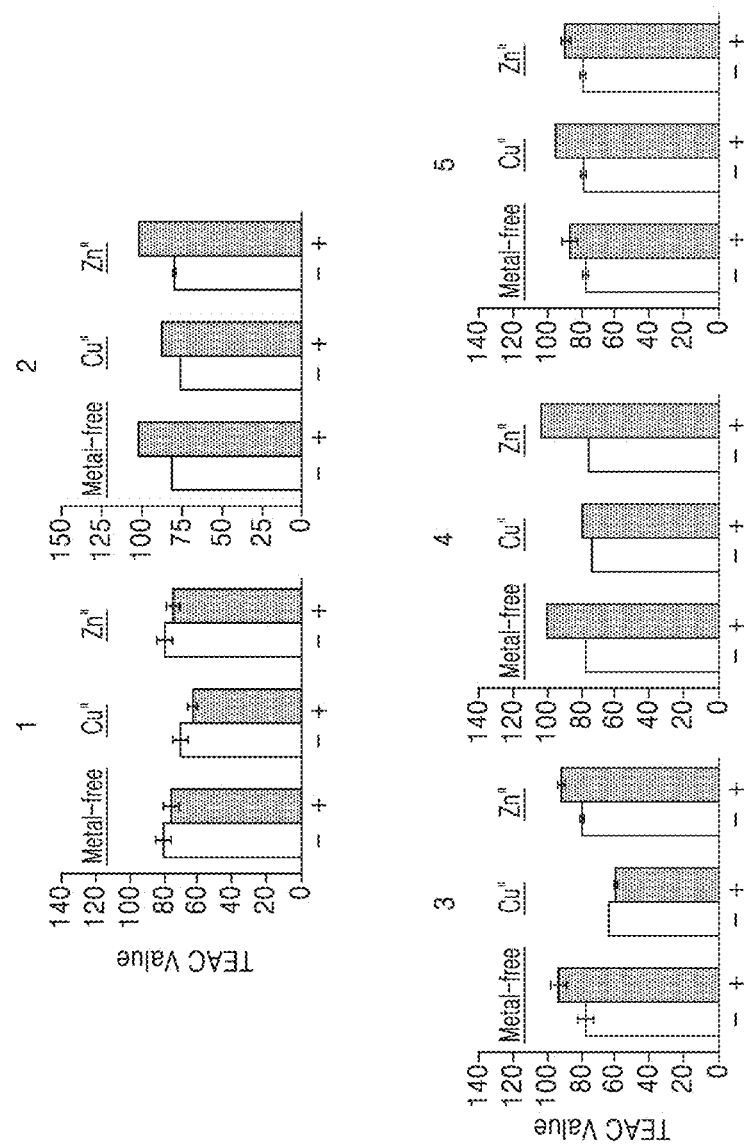
FIG. 4 shows cell-protecting effects of Compound 1 to Compound 5 with respect to cytotoxicity due to Aβ aggregates in the presence or absence of metals.

As a result, Compound 1 did not show excellent Aβ aggregation-inhibitory effect, irrespective of the presence of Aβ isoforms and metals. Compound 2 to Compound 5 showed different effects depending on the kinds of Aβ isoforms and metals, but most of them showed approximately 15% to 30% reduction in cytotoxicity which was caused by Aβ with metals or without metals (FIG. 4). Accordingly, it can be seen that the benzene diamine derivatives of the present disclosure may substantially inhibit cytotoxicity beyond the Aβ aggregation inhibitory and antioxidant effects, thereby increasing viability of neuronal cells.

5. Example 5: Preparation of Formulations Including Compound 2 to Compound 5

Formulations including the benzene diamine derivatives of the present disclosure may be prepared as follows. The following formulations are for the illustrative purpose only, and formulations including the compounds of the present disclosure as an active ingredient are not limited thereto.

5-1. Preparation Example 1: Preparation of Injectable Formulation

Each of Compound 2 to compound 5 (1 mg) of Example 1 was dissolved in distilled water for injection, and pH thereof was adjusted to about 6.8. Then, a total volume thereof was adjusted to 2 ml, and each solution was packed in a 2 ml ampule and sterilized to prepare injectable formulations.

5-2. Preparation Example 2: Preparation of Tablet

Each of Compound 2 to compound 5 (1 mg) of Example 1 was mixed with 100 mg of lactose, 100 mg or 50 mg of starch, and an appropriate amount of magnesium stearate, and tableted according to a common method of preparing a tablet, thereby preparing tablets.

5-3. Preparation Example 3: Preparation of Powder

Each of Compound 2 to compound 5 (1 mg) of Example 1 was mixed with 100 mg of lactose and 2 mg of magnesium stearate, and packed in polyethylene chloride-coated sheets and sealed to prepare powders.

5-4. Preparation Example 4: Preparation of Capsule

Each of Compound 2 to compound 5 (1 mg) of Example 1 was mixed with 50 mg of lactose, 50 mg or 93 mg of starch, 2 mg of talc, and an appropriate amount of magnesium stearate, and packed in gelatin capsules according to a common method of preparing a capsule, thereby preparing capsules.

6. Experimental Example 1: Morphological Change of Brain of Dementia Mouse Model In order to examine therapeutic effects of the benzene diamine derivatives on dementia, dementia mouse models were orally administered with the benzene diamine derivative, and morphological changes in the brains thereof were examined.

In detail, APP/PS/Tau was purchased as the dementia mouse model from Jackson lab (BAR HARBOR, USA), and APP/Tau female and APP/PSen1de9 purchased from Taconic (Hudson, USA) were cross-mated for 6 generations, and 4-month-old mouse models were obtained from F1. The dementia mouse models were divided into groups of 6 mice, and among the dementia mouse models, a control group was orally administered with a vehicle (PBS) for 2 months, and an experimental group was orally administered with 100 µg/kg/0.1 ml of $N^1$-(pyridin-2-ylmethyl)benzene-1,4-diamine (Compound 2) twice a week for 2 months. Thereafter, the mice were sacrificed, and their brains were removed. Their longitudinal sections were cut, and morphological changes were examined. For comparison, a normal mouse was sacrificed and its brain was removed. Its longitudinal section was cut, and morphological changes were examined.

Figure 6:
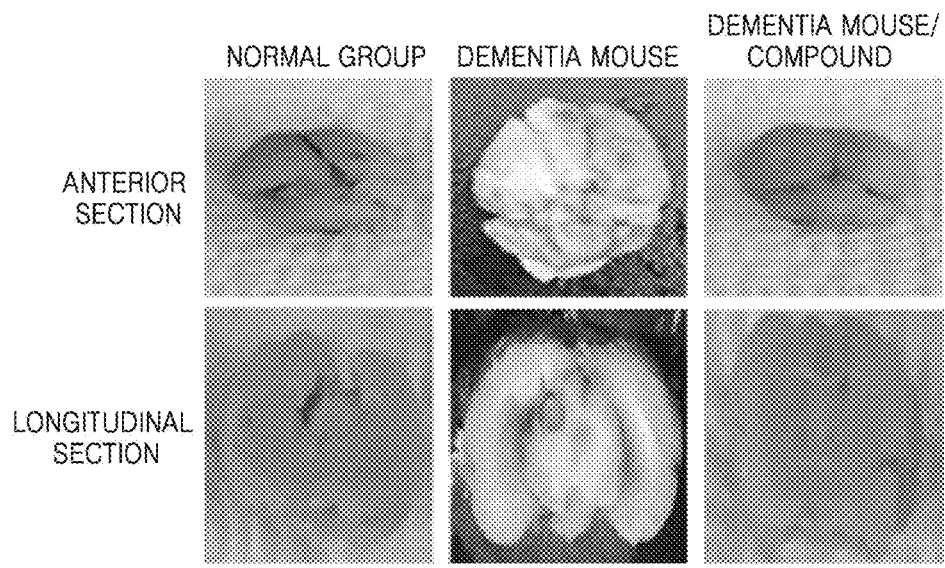
FIG. 6 shows images of morphological changes in the brains of dementia mouse models.

As a result, the control group (dementia mouse) showed bleeding in the morphology or longitudinal section of the brain whereas the experimental group orally administered with Compound 2 for 2 months showed the brain morphology similar to that of the normal group (FIG. 6). These results suggest that Compound 2 inhibited inflammation and angiogenesis caused by dementia factors, thereby preventing bleeding of the brain tissue and skin.

7. Experimental Example 2: Memory Capacity Change of Dementia Mouse Model

In order to investigate enhancement of spatial cognition and memory in dementia mouse models by the benzene diamine derivatives of the present disclosure, a Morris water maze (Harvard Apparatus, USA) test was performed.

In detail, a water maze composed of a stainless steel pool with a diameter of 150 cm×a height of 60 cm and an escape platform (10 cm in diameter, 30 cm in height) was filled with water at 22±2° C., and the height was 2 cm above the platform such that when a mouse sat on the escape platform, the body was allowed to come out of the water. Since the mouse searches for the escape platform using a marker around the water tank on the surface of the water tank, the marker was kept constant during the experiment so that the environment did not change. Escape latency was measured as the time taken for the experimental animal to go to the escape platform when the experimental animal went to the escape platform and stayed thereon for more than 20 seconds. This test was performed three times a day, and a mean value was determined as mean escape latency. The escape latency was recorded on the computer program (Smart Video Tracking System V3.0, PanLab SL, Barcelona, Spain) by installing a camera on the ceiling above the water tank.

The experiment was performed three times a day for 6 days, and at this time, the possibility of accidentally visiting the escape platform was minimized by sequentially changing the positions of the experimental animals in the water tank. In the experiment, a normal mouse, a control dementia mouse administered with a vehicle (PBS) and an experimental dementia mouse administered with 100 μg/kg of $N^1$-(pyridin-2-ylmethypenzene-1,4-diamine (Compound 2) twice a week for 2 months were used after completing administration, as in Experimental Example 1.

Figure 5:
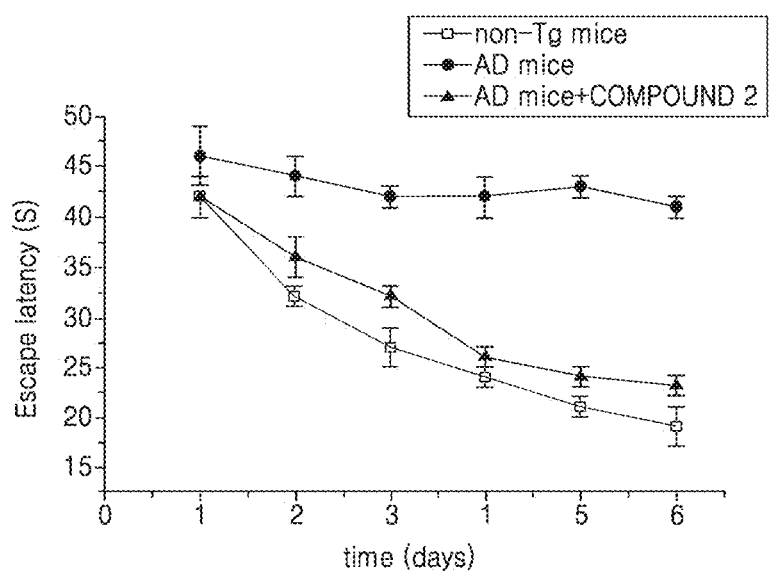
FIG. 5 shows escape latencies which represent behavioral changes of dementia mouse models in a water maze test.

As a result, as compared with the dementia control group, the Compound 2-treated group showed significantly short mean escape latency at 3 days, which was a similar level to that of the normal group (non-Tg mice), as shown in FIG. 5. The control group (AD mice) and the experimental group (AD mice+Compound 2) showed the mean escape latency of 42±1 sec and 26±1 sec at 4 days, respectively, and the difference was 16 sec. The dementia group and the Compound 2-treated group showed the mean escape latency of 43±1 sec and 24±1 sec at 5 days, respectively, and the difference was 19 sec, indicating statistically significant recovery of spatial cognition and memory. In particular, the normal group and the Compound 2-treated group showed a stable reduction graph after 4 days, clearly indicating long-term memory formation during the experimental period.

8. Experimental Example 3: Anatomical Change of Brain Tissue

Effects of the benzene diamine derivatives of the present disclosure on the recovery of dementia symptoms in dementia mouse models were examined by anatomical analysis of the brain tissue.

8-1. Examination of Inhibitory Effect on Monomeric Aβ Formation

Overexpression of monomeric Aβ may increase formation of oligomeric Aβ, Aβ aggregates, and amyloid plaques to cause neuronal cytotoxicity. Therefore, anatomical analysis of the brain tissue was performed to examine whether the benzene diamine derivatives of the present disclosure inhibit monomeric Aβ formation in dementia mouse models.

As in Experimental Example 1, a control group was orally administered with a vehicle for 2 months, and an experimental group was orally administered with 100 μg/kg/0.1 ml of $N^1$-(pyridin-2-ylmethyl)benzene-1,4-diamine (Compound 2) twice a week for 2 months. The brain was taken from a non-treated dementia mouse model (4 months), and the brains of the control group and the experimental group were also taken after the administration. Each mouse was anesthetized with ketamine, and then the skull was incised. The brain was then embedded in paraffin and subjected to immunohistofluorescence staining. The brain tissues were fixed in formalin and sectioned at a thickness of 50 μm by using a vibrotome, and each tissue was placed on a glass slice. For comparison of monomeric Aβ, BAM-10 monoclonal anti-Aβ primary antibody labeled with QD525 probe (green fluorescence) was used to examine changes in the quantity of monomeric Aβ42. Further, to measure changes of plaques, the tissues were stained with a fluorescent staining reagent MX04 (blue) and incubated at 4° C. for 12 hours. Thereafter, the tissues were observed under a confocal microscope at 0.5×10.

Figure 7:
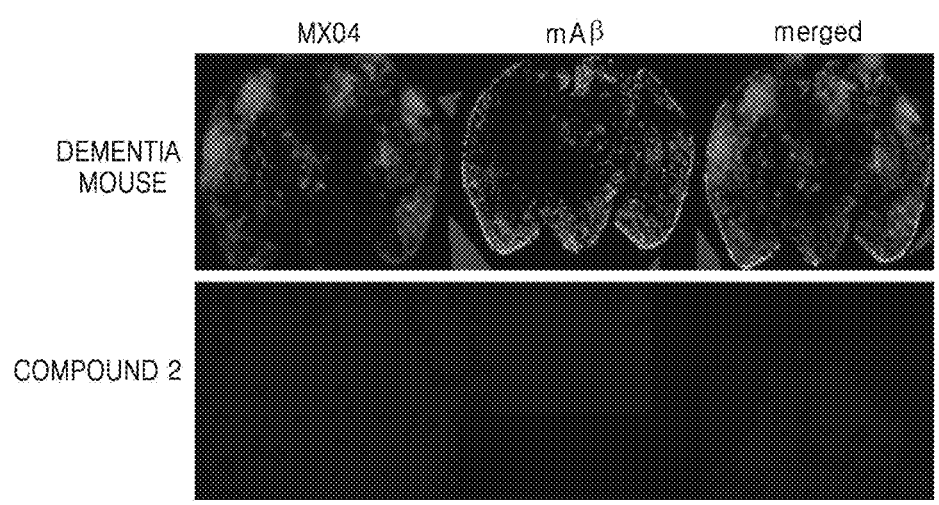
FIG. 7 shows confocal microscopic images of monomeric Aβ (mAβ) distribution in the brains of dementia mouse models.

As a result, as shown in FIG. 7, many plaques were observed in the entire brain, particularly, in the cortex and hippocampus of the non-treated control group (dementia mouse), whereas plaques were hardly observed in Compound 2-treated group. Further, a large amount of monomeric Aβ was observed in the control group, whereas monomeric Aβ formation was hardly observed in the cortex and hippocampus of the Compound 2-treated group. Accordingly, it can be seen that the benzene diamine derivatives, particularly, Compound 2 may inhibit excessive monomeric Aβ formation or plaque formation.

8-2. Examination of Inhibitory Effect on Oligomeric Aβ Formation

Oligomeric Aβ formation in the brain tissue may cause neuronal cell death by neuronal cytotoxicity, which may cause dementia. Therefore, anatomical analysis of the brain tissue was performed to examine whether the benzene diamine derivatives of the present disclosure inhibit neuronal cytotoxicity by oligomeric Aβ in dementia mouse models.

In detail, as in Experimental Example 7-1, the dementia mouse models were prepared and their brain tissues were stained. Anti-oligomeric Aβ primary antibody (ab126892, Abcam, Eugene, USA) labeled with QD525 probe (red fluorescence) was used to examine changes in the quantity of oligomeric Aβ42. Further, to measure changes of plaques, the tissues were stained with a fluorescent staining reagent MX04 (blue) and incubated at 4° C. for 12 hours. Thereafter, the tissues were observed under a confocal microscope at 0.5×10.

Figure 8:
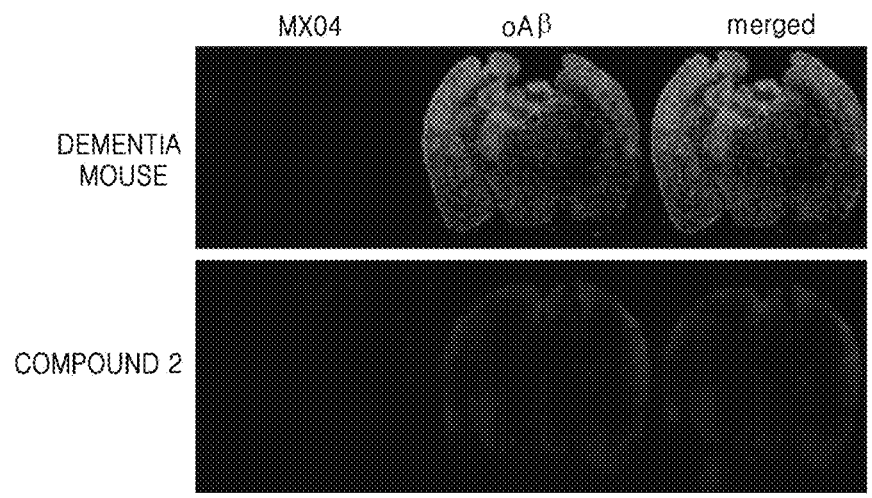
FIG. 8 shows confocal microscopic images of oligomeric Aβ (oAβ) distribution in the brains of dementia mouse models.

As a result, as shown in FIG. 8, a large amount of oligomeric Aβ was observed in the entire brain, particularly, in the cortex and hippocampus of the non-treated control group (dementia mouse), whereas oligomeric Aβ was hardly observed in Compound 2-treated group. Accordingly, it can be seen that the benzene diamine derivatives, particularly, Compound 2 may inhibit or reduce excessive oligomeric Aβ formation to inhibit neuronal cell death, thereby inhibiting neuronal cytotoxicity.

8-3. Examination of Inhibitory Effect on Aβ Aggregate Formation

Like oligomeric Aβ, Aβ aggregates in the brain tissue may cause neuronal cell death by neuronal cytotoxicity, which may cause dementia. Therefore, anatomical analysis of the brain tissue was performed to examine whether the benzene diamine derivatives of the present disclosure inhibit neuronal cytotoxicity by Aβ aggregates in dementia mouse models.

In detail, as in Experimental Example 7-1, the dementia mouse models were prepared and their brain tissues were stained. Aβ aggregates in the brain tissue were labeled with Thioflavin T (ThT, Sigma-Aldrich) (green fluorescence), plaques were stained with a fluorescent staining reagent MX04 (blue), and incubated at 4° C. for 12 hours. Thereafter, the tissues were observed under a confocal microscope at 0.5×10.

Figure 9:
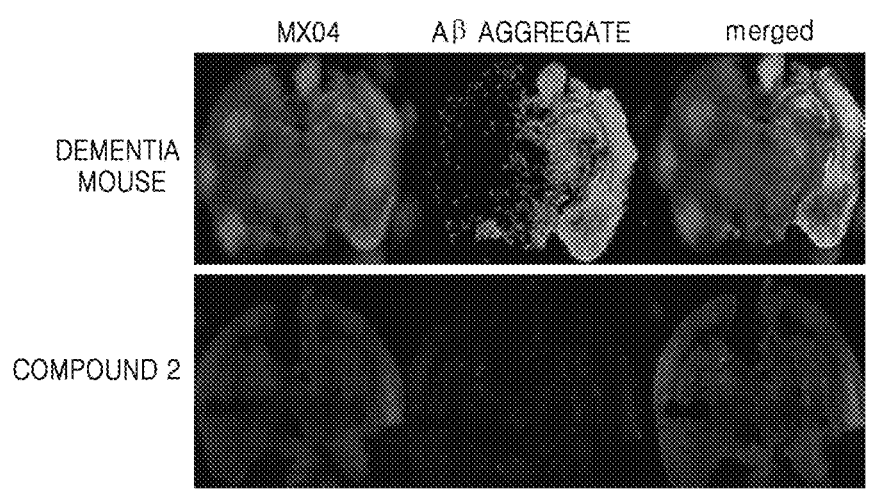
FIG. 9 shows confocal microscopic images of Aβ aggregate (ThT) distribution in the brains of dementia mouse models.

As a result, as shown in FIG. 9, a large amount of Aβ aggregates was observed in the entire brain, particularly, in the cortex and hippocampus of the non-treated control group (dementia mouse), whereas Aβ aggregates were hardly observed in Compound 2-treated group. Accordingly, it can be seen that the benzene diamine derivatives, particularly, Compound 2 may inhibit excessive Aβ aggregate formation or plaque formation.

9. Experimental Example 4: Examination of Cerebrovascular Permeability

In the selection of candidates for treating brain diseases, whether they are able to cross the brain-blood barrier (BBB) is important. Therefore, it was examined whether the benzene diamine derivatives of the present disclosure actually cross BBB to be absorbed into the brain.

Mice (CD1 female) were orally administered with 100 μg/kg/0.1 ml of the compound, and PAMPA-BBB analysis was performed by using a PAMPA Explorer kit (pION, Inc. Billerica, Mass., USA) according to the manufacture's protocol with slight modifications. Each stock solution was diluted with Prisma HT buffer (pH 7.4, pION) at a final concentration of 25 μM (final DMSO concentration of 1% v/v). The prepared solution was put in each well of a donor plate (200 μl, repeated 12 times). A polyvinylidene fluoride (PVDF, 0.45 μM) filter membrane on an acceptor plate was coated with BBB-1 lipid formulation (5 μl, pION). The acceptor plate was placed on top of the donor plate to generate a "sandwich". Brain sink buffer (BSB, 200 μl, pION) was added to each well of the acceptor plate. The sandwich-shaped plate was incubated for 4 hours at room temperature without stirring. UV-vis spectra of the solutions in the reference, acceptor, and donor plates were measured using a microplate reader. A PAMPA Explorer software [v. 3.8 (pION)] was used to calculate the –log Pe values for compounds. CNS±designations were assigned by comparison with compounds that were identified in previous reports.

The results are shown in the following Tables 2 and 3.

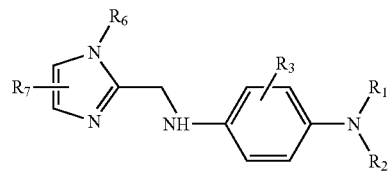
[Formula III]

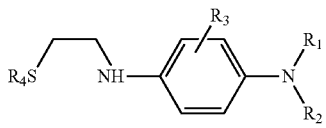
[Formula IV]

wherein, in Formula III or IV, $R_1$ and $R_2$ are each independently hydrogen or a substituted or unsubstituted $C_1$-$C_6$ alkyl group;

TABLE 2

| Administration dose (μg/kg) | Administraion mode | Time (h) | Matrix | Concentration (ng/ml or ng/g) Individual | | | Mean | SD | CV(%) |
| --- | --- | --- | --- | --- | --- | --- | --- | --- | --- |
| 100 | PO | 0.083 (5 min) | Plasma | 1076 | 92.8 | 2304 | 1158 | 1108 | 95.7 |
| | | | Brain | 44.3 | 34.0 | 200 | 92.8 | 93.0 | 100 |
| | | | CSF | 146 | 205 | 594 | 315 | 243 | 77.3 |

TABLE 3

| Test | Concentration | Incubation time | Pe (10⁻⁶ cm/sec) | BCS code | Method |
| --- | --- | --- | --- | --- | --- |
| Progesterone | 50 μM | 4 hrs | 46.699 | High (CNS+) | U.V |
| Lidocaine | 50 μM | 4 hrs | 24.698 | High (CNS+) | U.V |
| Theophylline | 50 μM | 4 hrs | 0.174 | Low (CNS−) | U.V |
| Compound 2 | 50 μM | 4 hrs | 12.471 | High (CNS+) | U.V |

$R_3$ is hydrogen, a halogen, a hydroxy group, a substituted or unsubstituted amine, a substituted or unsubstituted $C_1$-$C_6$ alkyl group, or a substituted or unsubstituted $C_1$-$C_6$ alkoxy group;

$R_7$ is hydrogen, a halogen, a hydroxy group, an amine, a $C_1$-$C_6$ alkyl group, or a $C_1$-$C_6$ alkoxy group;

$R_6$ is hydrogen or a $C_1$-$C_6$ alkyl group;

$R_4$ is hydrogen or a substituted or unsubstituted $C_1$-$C_6$ alkyl group; and a substituent is selected from the group consisting of a halogen, a $C_1$-$C_6$ linear or branched alkyl group, a $C_1$-$C_6$ alkoxy group, a hydroxy group, an amine, a $C_1$-$C_6$ alkylamine group, a nitro group, an amide, a $C_1$-$C_6$ alkylamide, urea, and an acetyl group.

2. The method of claim 1, wherein in Formulae III and IV, $R_1$ and $R_2$ are each independently a substituted or unsubstituted $C_1$-$C_6$ alkyl group.

3. The method of claim 1, wherein the compound is represented by one of the following Formulae:

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of treating dementia or Alzheimer's disease, the method comprising administering a compound represented by the following Formula III or IV, or a solvate, stereoisomer, or pharmaceutically acceptable salt thereof to a subject in need thereof:

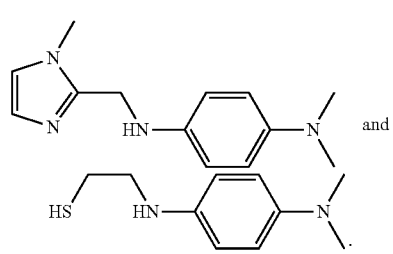

* * * * *